United States Patent
Vyas et al.

(10) Patent No.: US 12,070,238 B2
(45) Date of Patent: Aug. 27, 2024

(54) TETHERED LAPAROSCOPIC PROBE GRIP

(71) Applicant: LIGHTPOINT MEDICAL, LTD, Amersham (GB)

(72) Inventors: Kunal Vyas, Amersham (GB); Gavin Ryan, Amersham (GB); David Tuch, Amersham (GB); Stewart Forbes, Amersham (GB); Francesca Oldfield, Amersham (GB)

(73) Assignee: Lightpoint Surgical Ltd, Amersham (GB)

( * ) Notice: Subject to any disclaimer, the term of this patent is extended or adjusted under 35 U.S.C. 154(b) by 836 days.

(21) Appl. No.: 17/152,653

(22) Filed: Jan. 19, 2021

(65) Prior Publication Data

US 2021/0161549 A1 Jun. 3, 2021

Related U.S. Application Data

(63) Continuation of application No. PCT/GB2019/052055, filed on Jul. 23, 2019.

(30) Foreign Application Priority Data

Jul. 25, 2018 (GB) ..................................... 1812131

(51) Int. Cl.
*A61B 17/29* (2006.01)
*A61B 17/00* (2006.01)

(52) U.S. Cl.
CPC .... *A61B 17/29* (2013.01); *A61B 2017/00079* (2013.01); *A61B 2017/00106* (2013.01); *A61B 2017/2926* (2013.01); *A61B 2562/04* (2013.01)

(58) Field of Classification Search
CPC .......... A61B 17/29; A61B 2017/00079; A61B 2017/00106; A61B 2017/2926;
(Continued)

(56) References Cited

U.S. PATENT DOCUMENTS

2012/0238879 A1 9/2012 Sasady
2013/0018388 A1 1/2013 Oko et al.
(Continued)

FOREIGN PATENT DOCUMENTS

CN 104688275 A 6/2015
GB 2570730 A 8/2019
(Continued)

OTHER PUBLICATIONS

CN201980049629.6, "Office Action", Oct. 16, 2023, 9 pages.
(Continued)

*Primary Examiner* — Joel Lamprecht
(74) *Attorney, Agent, or Firm* — Kilpatrick Townsend & Stockton LLP (57) ABSTRACT

A tethered laparoscopic probe for deployment through a trocar into a cavity of a subject and manipulatable by fenestrated laparoscopic graspers includes opposing fenestrated jaws. The tethered laparoscopic probe also includes a probe head shaped for insertion through the trocar and including an elongated casing, a sensor arranged within the casing and defining a sensing direction of the probe head, and a grip for secure grasping by the fenestrated laparoscopic graspers. The grip has protrusions for mating with the fenestrated jaws. The tethered laparoscopic probe further includes a tether coupled to the probe head. The protrusions are positioned and shaped to enable the grip to be grasped securely by the fenestrated laparoscopic graspers at a first angle relative to the sensing direction of the probe head and at a second angle relative to the sensing direction of the probe head, the second angle being different from the first angle.

19 Claims, 8 Drawing Sheets

(58) Field of Classification Search
CPC . A61B 2562/04; A61B 6/4266; A61B 6/4405; A61B 6/4241; A61B 8/4218; A61B 6/4258; A61B 6/4429; A61B 8/12; A61B 8/4455; A61B 90/37; A61B 2090/378; A61B 17/00234; A61B 2017/00283; A61B 6/425; A61B 6/4452; A61B 2017/2927; A61B 2017/2929
See application file for complete search history.

(56) References Cited

U.S. PATENT DOCUMENTS

| | | | |
|---|---|---|---|
| 2014/0309529 A1 | 10/2014 | O'Neill et al. | |
| 2015/0157293 A1* | 6/2015 | Shibamoto | A61B 8/12 600/462 |
| 2016/0266260 A1* | 9/2016 | Preston | G01T 1/208 |

FOREIGN PATENT DOCUMENTS

| | | |
|---|---|---|
| JP | 2016077367 A | 5/2016 |
| WO | 2015185665 A1 | 12/2015 |
| WO | PCT/GB2019/051463 | 5/2019 |

OTHER PUBLICATIONS

Machine Translation of CN201980049629.6, "Office Action", Oct. 16, 2023, 17 pages.
EP19748895.0, "Communication for Party to Proceedings/Third Party", Jan. 2, 2023, 2 pages.
GB1808728.8, "Request for Grant of a Patent", May 29, 2018, 2 pages.
GB1812131.9, "Combined Search and Examination Report", Jan. 28, 2019, 6 pages.
PCT/GB2019/052055, "International Search Report and Written Opinion", Oct. 1, 2019, 24 pages.

* cited by examiner

TETHERED LAPAROSCOPIC PROBE GRIP

CROSS-REFERENCES TO RELATED APPLICATIONS

This application claims priority to and is a continuation of International Patent Application No. PCT/GB2019/052055, filed Jul. 23, 2019, which claims priority from GB Patent Application No. 1812131.9, filed Jul. 25, 2018, the entire contents of which are hereby incorporated by reference in their entirety for all purposes.

TECHNICAL FIELD

The present disclosure relates to laparoscopic probes. In particular, the present disclosure relates to a tethered laparoscopic probe to be inserted into a cavity via a trocar. The present disclosure further concerns grips for tethered laparoscopic probes.

BACKGROUND OF THE INVENTION

Laparoscopic surgery, also called minimally-invasive surgery or keyhole surgery, is a surgical technique in which operations are performed using a small incision (usually 0.5-1.5 cm) in the body of a subject. Laparoscopic surgery provides a host of clinical benefits over open surgery, for example pain and hemorrhaging are reduced due to smaller incisions, and recovery times for the patient are reduced.

In order to perform laparoscopic surgery on a subject, a small incision is made in the body of the subject and a trocar is placed into the incision. A trocar is a medical device that acts as a portal for the subsequent placement of other instruments into a cavity of the subject for use in the surgery. The size of the trocar, for example the diameter of the trocar, provides a limit on the size of the instrument(s) that can be used in the laparoscopic surgery, as the instruments need to be able to pass through the trocar into the subject. For some types of laparoscopic surgeries, multiple instruments may be required—if these instruments are required at the same time and each take up a port, then multiple incisions may be required, leading to patient discomfort and slower patient recovery times.

Many laparoscopic probes typically comprise a detector supported by a rigid rod, which may be inserted through a trocar into a cavity of a subject. However, such probes have limited maneuverability within the cavity due to the restriction of movement of the rigid rod within the trocar. Furthermore, such laparoscopic probes would use up an entire trocar, and so further incisions in the subject would be required if further surgical tools are required for the surgery.

The present application provides solutions to overcome problems such as those described above.

SUMMARY OF THE INVENTION

According to an aspect of the present disclosure, a tethered laparoscopic probe is provided. The tethered laparoscopic probe is suitable for deployment through a trocar into a cavity of a subject. The tethered laparoscopic probe is manipulatable by fenestrated laparoscopic graspers comprising opposing fenestrated jaws. The tethered laparoscopic probe comprises a probe head shaped for insertion through the trocar. The probe head comprises an elongated casing. The probe head further comprises a sensor arranged within the casing, the sensor defining a sensing direction of the probe head. The probe head further comprises a grip for secure grasping by the fenestrated laparoscopic graspers, the grip comprising protrusions for mating with the fenestrated jaws. The tethered laparoscopic probe further comprises a tether coupled to the probe head and for, in use, tethering the probe head through the trocar. The protrusions are positioned and shaped to enable the grip to be grasped securely by the fenestrated laparoscopic graspers at a first angle relative to the sensing direction of the probe head. The protrusions are positioned and shaped to enable the grip to be grasped securely by the fenestrated laparoscopic graspers at a second angle relative to the sensing direction of the probe head, the second angle different to the first angle.

By providing such a tethered laparoscopic probe, the laparoscopic probe may be deployed through a port of a trocar and, in use, not take up the entire capacity of the port. Accordingly, further instrument(s) may be used with the same trocar port while the laparoscopic probe is deployed. Further advantageously, in comparison to traditional laparoscopic probes which comprise a rigid rod-like structure limiting control of a detector head to four degrees of freedom, a tethered laparoscopic probe as described herein may, in use, have six degrees of freedom.

Laparoscopic graspers, also known as tissue graspers or forceps, are a form of grasping instrument usually used to manipulate delicate tissue during laparoscopic procedures. One of their many functions is to facilitate adequate access to the surgical site by holding tissue clear of the operating field. Modern laparoscopic graspers are typically manufactured from surgical grade stainless steel, and may also incorporate other materials including titanium, tungsten carbide and various plastics. Laparoscopic graspers are one of a range of laparoscopic tools that differ from their conventional surgical counterparts in that they have an extended shaft or stylus in order that they can be maneuvered through small incisions during minimally invasive procedures. Such laparoscopic graspers can be reusable or disposable.

Laparoscopic graspers, as described herein, typically comprise a pair of opposing jaws at the end of the shaft or stylus that is to be inserted into the cavity. The jaws can be opened or closed in order to release or grasp tissue or other objects. The inner surfaces of such teeth may be profiled with waves, teeth, protruding hemispheres or cross-serrated ribbing. The inner surfaces may be smooth. Several types of jaw are available, including straight or flared, traumatic or atraumatic, single or dual-action, and fenestrated or solid. Fenestrated designs incorporate an open area or window into one or both jaws, making them lighter, and may offer a safer grip than friction alone by enclosing a portion of tissue within the window. The term "fenestrated laparoscopic graspers" or "fenestrated grasping forceps" as used herein refers to laparoscopic graspers having a pair of fenestrated laparoscopic jaws i.e. two jaws, each of which has located in it a gap, window, open area or slot. The slots may be of any suitable shape. For example, the slots may be rectangular or oblong. Such fenestrated laparoscopic jaws may be manually operable, for example Johan graspers. Such fenestrated laparoscopic graspers may be operable by a processor or robotics system.

The term "sensing direction" is used herein to denote a direction of reference only, as would be understood by the person skilled in the art. In some embodiments, the sensor may be a directional sensor, in which case the sensing direction may be defined as the direction in which the sensor is directed; however, the sensing direction may be any other direction defined with reference to the sensor. Similarly, in some embodiments the sensor may comprise a multi- or omni-directional sensor, and the "sensing direction" may be any direction defined with reference to the sensor—the sensing direction is for reference purposes.

Advantageously, the tethered laparoscopic probe provides protrusions positioned and shaped to enable the grip to be grasped securely by the fenestrated laparoscopic graspers at a first angle relative to the sensing direction of the probe head, and at a second angle relative to the sensing direction of the probe head, the second angle different to the first angle. In this way, a user (whether human or processor) of the fenestrated laparoscopic graspers is able to grasp the probe securely with at least two angles of engagement—that is, angles relative to the sensing direction. In the confined spaces in which laparoscopic surgery is performed, such an ability to securely hold the probe at a variety of angles is invaluable as it allows for better manipulation of the probe within the cavity.

In the context of the present disclosure, the fenestrated laparoscopic graspers may grasp "securely" the probe head of the laparoscopic probe when the jaws of the graspers engage with the probe head such that unintentional rotational movement away from the angle of engagement is greatly inhibited.

As the tethered laparoscopic probe is for deployment into a cavity, it is necessary that the probe head is small enough to pass through a port of a trocar, which may be, for example, 12 mm in diameter. Typically, a trocar will have a diameter of around 12 mm, although in recent years trocars are often used which have diameters of 10 mm of smaller. The diameter of the probe head, and therefore the components therein, must be small enough to pass through the trocar.

The grip may be beveled. The grip may be magnetic.

The elongated casing may comprise one or more of tungsten (with a biocompatible coating applied), stainless steel, tantalum and plastic.

The protrusions may comprise a pair of protrusions positioned such that the first protrusion of the pair of protrusions is graspable by a first jaw of the fenestrated laparoscopic graspers while a second protrusion of the pair of protrusions is graspable by a second jaw of the fenestrated laparoscopic graspers. The pair of protrusions may be positioned and shaped to be graspable securely by the fenestrated laparoscopic graspers at the first angle. The pair of protrusions may be positioned and shaped to be graspable securely by the fenestrated laparoscopic graspers at the second angle.

In one or more embodiments, the first angle and the second angle may be substantially perpendicular to one another. For example the first angle may be substantially 0 degrees and the second angle may be substantially 90 degrees to the sensing direction.

The protrusions may comprise a first pair of protrusions and a second pair of protrusions. A first protrusion of the first pair of protrusions may be positioned and shaped to be graspable by a first jaw of the fenestrated laparoscopic graspers at the first angle, and a second protrusion of the first pair of protrusions may be positioned and shaped to be graspable by a second jaw of the fenestrated laparoscopic graspers at the first angle. A first protrusion of the second pair of protrusions may be positioned and shaped to be graspable by the first jaw of the fenestrated laparoscopic graspers at the second angle, and a second protrusion of the second pair of protrusions may be positioned and shaped to be graspable by the second jaw of the fenestrated laparoscopic graspers at the second angle. The first angle and the second angle may or may not be perpendicular to each other. The first angle may be substantially 105 degrees relative to the sensing direction. The second angle may be substantially 60 degrees relative to the sensing direction.

The protrusions may be positioned and shaped to enable the grip to be graspable by the fenestrated laparoscopic graspers at a third angle relative to the sensing direction of the probe head, the third angle different to the first angle and the second angle. Advantageously, this would enable a user to manipulate the probe still further within the cavity.

The grip may further comprise a rib. The rib may be grippable by jaws of a surgical instrument. The rib may separate adjacent recesses of the grip. The surgical instrument may comprise a needle driver or needle holder.

Advantageously, the rib enables a user to hold the tethered laparoscopic probe in place within the cavity with the e.g. needle driver, while releasing the grip of the fenestrated laparoscopic graspers to adjust the angle of engagement from the first angle to the second angle (or vice versa). As the probe head is for insertion through a trocar, it is beneficial to provide the recesses around the rib in order to provide a grippable area without substantially increasing the diameter of the probe head.

The tethered laparoscopic probe may further comprise a collar grip fitted to the tether. The collar grip may be grippable by jaws of a surgical instrument. The surgical instrument may comprise a needle driver. Once again, the collar grip enables the user to hold the tethered laparoscopic probe in place within the cavity while releasing the grip of the fenestrated laparoscopic graspers to adjust the angle of engagement from the first angle to the second angle (or vice versa). The collar grip further allows manipulation of the tether itself without running the risk of requiring the user to directly contact the tether with the surgical instrument, which may result in damage to the tether.

The sensor may comprise a gamma radiation detector configured to detect gamma radiation through an aperture of the casing. The gamma radiation detector may comprise a scintillator configured to scintillate, in use, in response to received gamma radiation. A scintillator is a material that exhibits scintillation (luminescence) in response to ionizing radiation; when struck by a charged particle, the scintillator absorbs the energy of the charged particle and re-emits energy in the form of light. The gamma radiation detector may further comprise a photodetector to detect the scintillated light from the scintillator. The photodetector may comprise a silicon photomultiplier ("SiPM"). The photodetector may comprise an avalanche photodiode ("APD"). The scintillator may comprise Thallium activated Cesium Iodide, CsI:Tl. The scintillator may be silvered on one or more surfaces, for example on a circumferential face of the scintillator or a face of the scintillator closest to the detection end of the laparoscopic probe, to reflect scintillated light towards the photodetector. This advantageously results in better signal collection and is also useful for achieving a good energy resolution.

The aperture may be a hole or gap in the casing, or may comprise a window. The window may comprise plastic or polyethylene terephthalate (PET).

By providing a gamma radiation detector, the laparoscopic probe may be used for radioguided laparoscopic procedures. A subject may receive a radiopharmaceutical in advance of surgery, the radiopharmaceutical designed to locate abnormal tissue such as tumors in the subject and to emit radiation detectable by the probe. A radiopharmaceutical is a drug that can be used for diagnostic or therapeutic purposes and comprises a radioisotope bonded to a molecule. The radiopharmaceutical conveys the isotope to specific organs, tissues or cells, and is selected for its properties and purpose. Many radiopharmaceuticals are known in the art and are used for radioguided surgery and other procedures. The tethered laparoscopic probe may therefore be inserted through a trocar into a cavity of the subject in an attempt to locate the source of the radiation and thereby locate any abnormal tissue.

The probe head may further comprise radiation shielding, either as part of or within the casing for inhibiting gamma radiation from passing through the probe head. The radiation shielding may comprise tungsten. The radiation shielding may have a thickness, and the scintillator may have a radius, and the thickness of the radiation shielding and the radius of the scintillator may be selected such that, in use, the ratio of the gamma radiation permeating through the radiation shielding that is detected by the gamma detection means to the gamma radiation incident on the radiation shielding is less than or equal to 1:1000, and such that, in use, the sensitivity of the gamma detection means to gamma radiation incident through the detection aperture is maximized. By providing such radiation shielding and scintillator, the ability of the probe to locate the source of radiation is greatly improved as such a ratio is suitable to assure a user that any detected radiation came from a known direction (e.g. the sensing direction) as opposed to passing through any other part of the probe head. Accordingly, such radiation shielding enables better directional resolution of the device. The aperture may comprise a designed gap or hole in the radiation shielding.

The gamma radiation detector may comprise a semiconductor gamma radiation detector. The semiconductor radiation detector may comprise Cadmium Zinc Telluride, CZT.

The sensor may comprise a beta radiation detector configured to detect beta radiation through an aperture of the casing. The beta radiation detector may comprise a scintillator configured to scintillate, in use, in response to received beta radiation. The beta radiation detector may further comprise a photodetector to detect the scintillated light from the scintillator. The scintillator configured to scintillate in response to received beta radiation may comprise cesium iodide, CsI. The scintillator configured to scintillate in response to received beta radiation may comprise fluorophore doped vinyltoluene.

Advantageously, by providing such a beta radiation detector in the tethered laparoscopic probe, the laparoscopic probe is enabled to pick up further signatures of a radioisotope. Furthermore, charged particles from radiopharmaceuticals do not travel far through tissue and so, using a beta radiation detector, one may determine that the radiation source is close (and therefore a tumor is close) when charged particles are detected. Some beta decaying radioisotopes, including Fluorine-18 (18F), Carbon-11 (11C), Nitrogen-13 (13N), Copper-64 (64Cu), Iodine-124 (124I) and Gallium-68 (68Ga), emit positrons during radioactive decay and are known to be used in positron emission tomography imaging. Some beta decaying radioisotopes, including tritium (3H), Carbon-14 (14C), and Silicon-35 (35S), emit electrons during radioactive decay. Some radiopharmaceuticals are primarily gamma radiation emitters but may also emit charged particles. For example, Technetium-99m (99mTc) is a gamma radiation emitter, but through a process of internal conversion emits K, L or M shell electrons for approximately 10% of decays.

The sensor may comprise an ultrasound sensor. Advantageously, this would enable the tethered laparoscopic probe to be used to take ultrasound readings.

The probe head may further comprise a second sensor arranged within the casing, the second sensor for sensing through an aperture of the casing. By providing multiple sensors, the probe may be used to detect multiple signals.

The second sensor may be different to the first sensor. For example, the probe may comprise a gamma radiation detector and a beta radiation detector.

The second sensor may be of the same type as the first sensor. For example, the tethered laparoscopic probe may comprise two gamma radiation detectors. Advantageously, by providing two such gamma radiation detectors, the laparoscopic probe is capable of "active collimation". The signals from both detectors may be used to extract directional information on detected gamma radiation, and accordingly the signal to noise ratio of the laparoscopic probe is greatly increased.

The laparoscopic probe may be arranged to communicate a composite signal, the composite signal representative of detections of both sensors. The laparoscopic probe may be switchable between a first mode, in which the probe head configured to communicate a first signal representative of a detection using the first sensor, and a second mode, in which the probe head is configured to communicate a second signal representative of a detection using the second sensor.

The grip may be structurally integral/intrinsic to the casing. That is, the grip may be a feature of the casing. The grip may alternatively be a modular addition to the casing.

According to an aspect of the present disclosure, a tethered laparoscopic probe for deployment through a trocar into a cavity of a subject is provided. The tethered laparoscopic probe comprises a probe head shaped for insertion through the trocar. The probe head comprises an elongated casing. The probe head further comprises a sensor arranged within the casing, the sensor defining a sensing direction of the probe head. The tethered laparoscopic probe further comprises a tether coupled to the probe head and for, in use, tethering the probe head through the trocar. The tethered laparoscopic probe further comprises a collar grip fitted to the tether, the collar grip grippable by jaws of a surgical instrument.

Advantageously, such a tethered laparoscopic probe is highly versatile and manipulatable.

According to an aspect of the present disclosure, a kit is provided. The kit comprises a tethered laparoscopic probe as described herein. The kit further comprises fenestrated laparoscopic graspers comprising opposing fenestrated jaws, the fenestrated jaws shaped to mate with protrusions of the grip of the tethered laparoscopic probe to securely grasp the tethered laparoscopic probe.

The fenestrated laparoscopic graspers may be any suitable graspers for grasping the probe. The fenestrated laparoscopic graspers may be robotically controllable. The fenestrated laparoscopic graspers may be manually controllable. For example, the fenestrated laparoscopic graspers may comprise Johan graspers.

BRIEF DESCRIPTION OF THE DRAWINGS

Embodiments of the invention will now be described by way of example only, with reference to the accompanying figures, in which.

Throughout the description and the drawings, like reference numerals (sometimes with an apostrophe or prime symbol) refer to like parts.

DETAILED DESCRIPTION OF THE INVENTION

Figure 1:
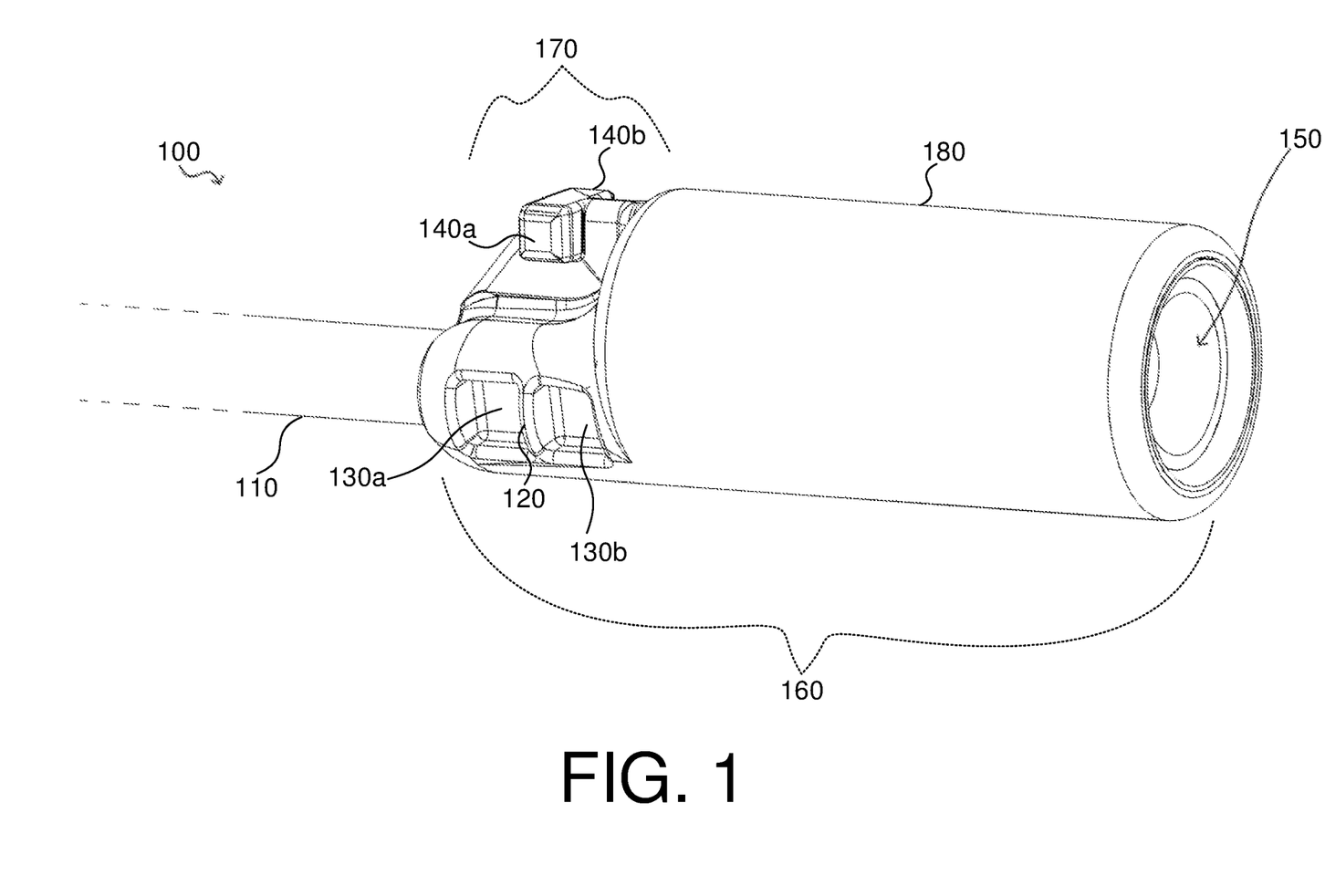
FIG. 1 illustrates a first example of a tethered laparoscopic probe from a first perspective.
Figure 2:
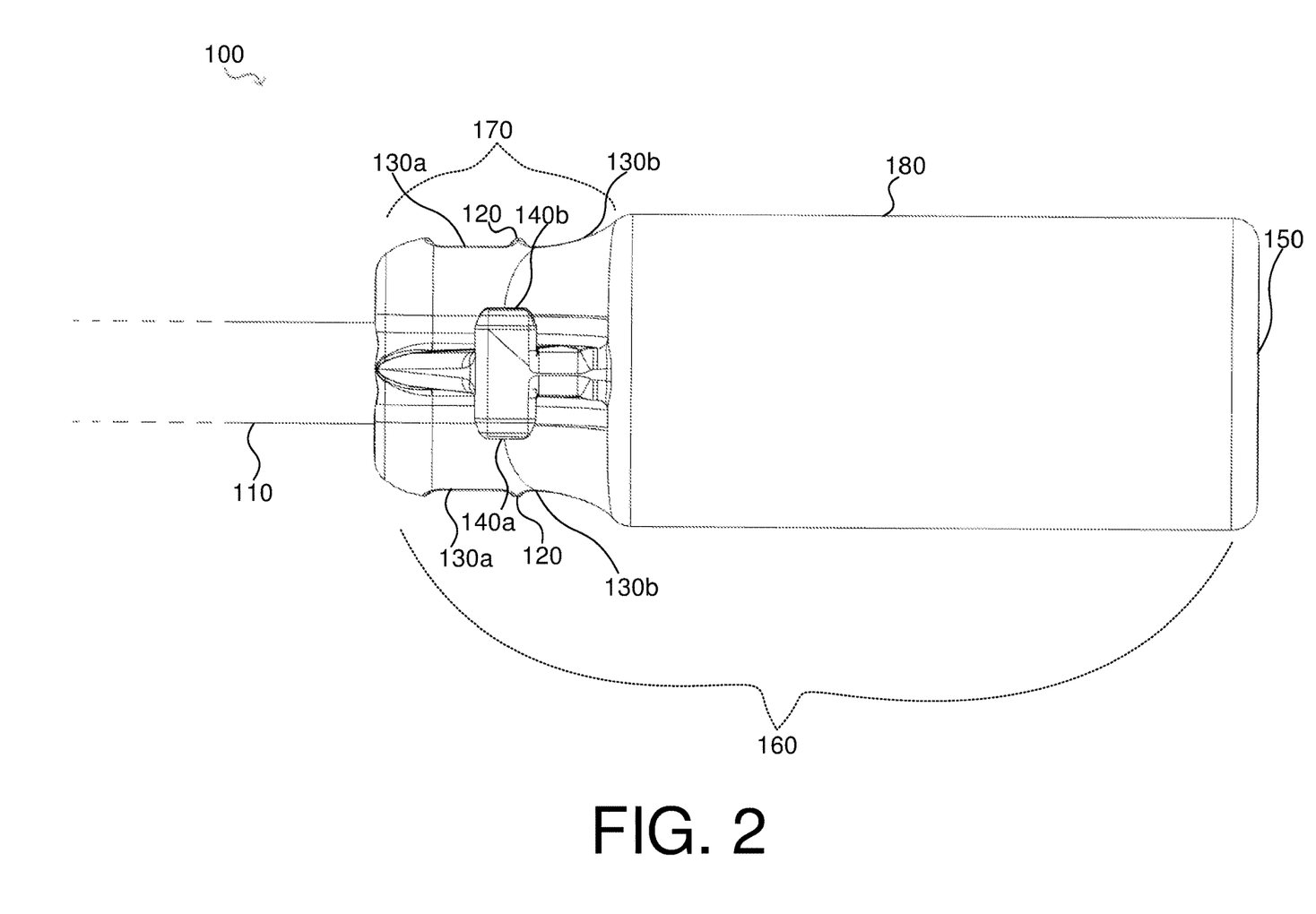
FIG. 2 shows the tethered laparoscopic probe of FIG. 1 from a second perspective.

FIG. 1 illustrates a tethered laparoscopic probe 100 from a first perspective. FIG. 2 shows the tethered laparoscopic probe 100 of FIG. 1 from a second perspective.

Figure 3:
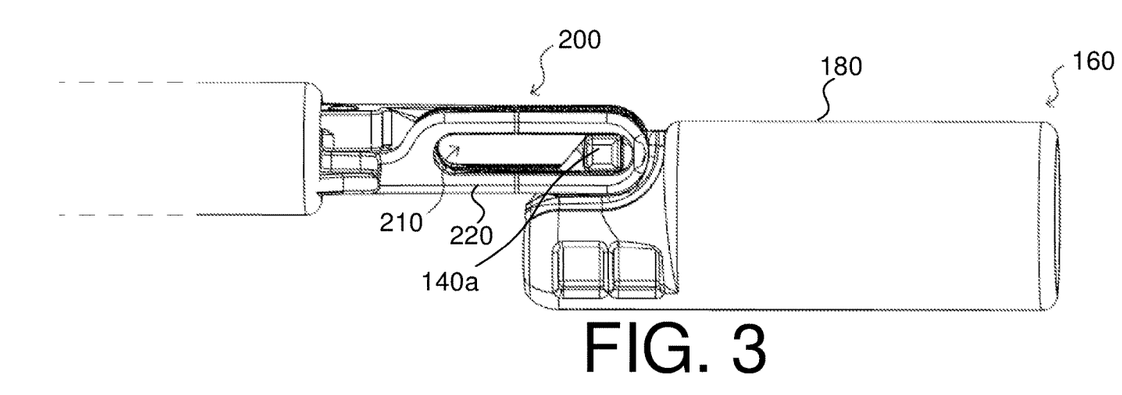
FIG. 3 shows the probe head of the tethered laparoscopic probe of FIG. 1 being held with fenestrated laparoscopic graspers at a first angle.
Figure 4:
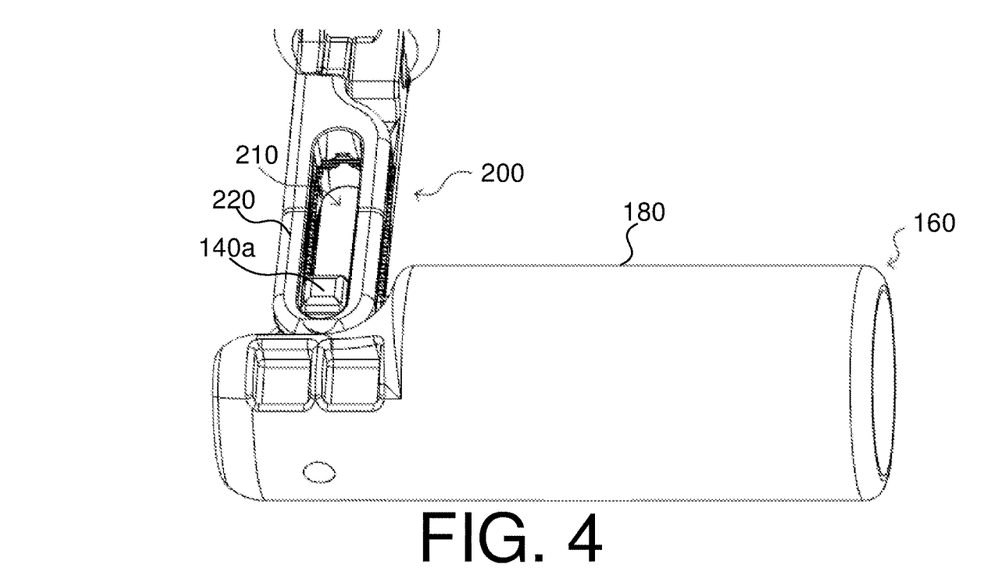
FIG. 4 shows the probe head of the tethered laparoscopic probe of FIG. 1 being held with fenestrated laparoscopic graspers at a second angle.
Figure 5:
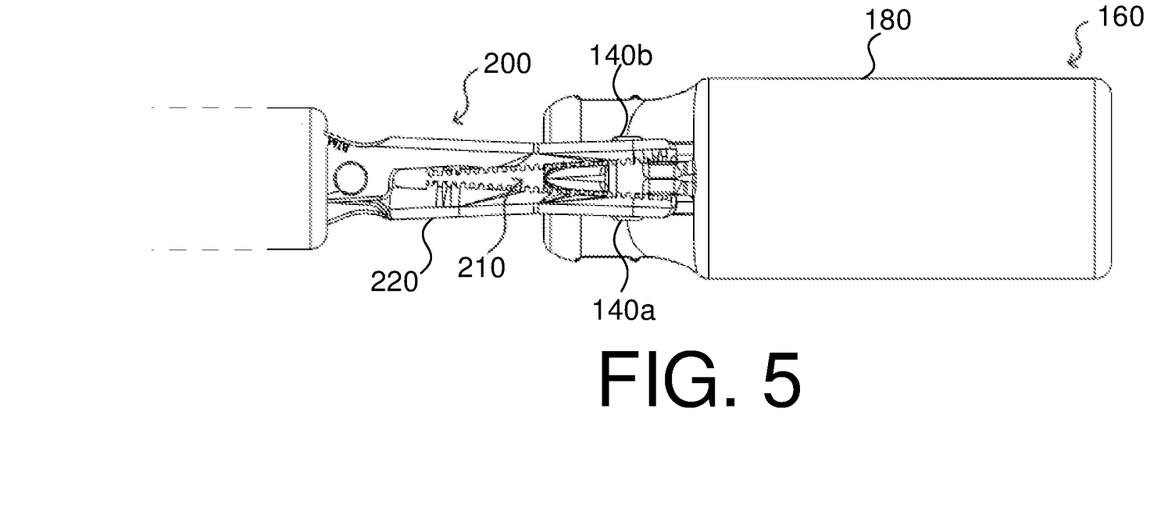
FIG. 5 shows the probe head of the tethered laparoscopic probe of FIG. 1 being held with fenestrated laparoscopic graspers at the first angle.

The tethered laparoscopic probe 100 comprises a probe head 160 and a tether 110. FIGS. 3 and 5 show the probe head 160 held at a first angle relative to a sensing direction of the probe head 160. FIG. 4 shows the probe head 160 held at a second angle relative to the sensing direction of the probe head 160. The tether 110 is not shown in FIG. 3, 4 or 5 for clarity of illustration only.

The probe head 160 comprises an elongated casing 180 comprising a biocompatible material. The probe head 160 further comprises a sensor (not shown) arranged within the casing 180. The sensor may comprise any suitable type of sensor. In the embodiment shown in FIGS. 1 to 5, the sensor is a gamma radiation detector or a beta radiation detector, although the skilled person would appreciate that any other type of sensor that can fit within the probe head 180 may be used.

In the embodiment shown in FIG. 1, an aperture 150 is positioned at a distal end of the casing 180 (that is, at an end of the probe head 160 located away from the tether 110). The sensor, a gamma radiation detector or a beta radiation detector, is arranged to sense through the aperture 150 of the probe head 160. For example, if the sensor comprises a gamma radiation detector then the sensor may detect gamma radiation that passes through the aperture 150 of the casing 180. If the sensor comprises a beta radiation detector then the sensor may detect beta radiation that passes through the aperture 150 of the casing 180.

The casing 180 may comprise radiation shielding to inhibit gamma (or beta) radiation from passing through the casing 180, so that a user of the tethered laparoscopic probe 100 can determine that radiation sensed by the sensor was detected through the aperture 150 of the casing 180. The radiation shielding may comprise tungsten or tantalum.

The skilled person would appreciate that in other embodiments, the sensor may be configured to sense through a side of the elongated casing 180. The aperture 150 may or may not be present. If present, the aperture 150 may be positioned in the side of the casing 180.

The aperture 150 may comprise a hole, an opening or a vacant space in the casing 180—that is, an area of space not covered by the opaque casing 180. The aperture 150 may comprise a window in the casing 180. The window may be permeable/transparent/transmissive to the radiation of interest, be it gamma radiation or beta radiation, and so may permit gamma (or beta) radiation to pass into the probe head 160 to be detected by the sensor. The thickness of the window may be selected to be suitable for the radiation being measured, for example the window may be very thin when the radiation of interest is beta radiation. The window may be formed from any suitable material, for example a plastic or polyethylene terephthalate (PET).

The sensor defines a sensing direction of the probe head 160. The skilled person would appreciate that the term sensing direction here is to be interpreted broadly. For exemplary purposes only, the sensing direction of the probe head 160 of FIGS. 1-5 is considered to be the transversal direction of the elongated casing 180, passing through the aperture 150.

The tether/connecting portion may comprise a biocompatible casing and one or more optical fibers for communicating to a computing device (not shown).

The outer casing 180 is biocompatible. The outer casing 180 may comprise one or more of tungsten (with a biocompatible coating applied), stainless steel, tantalum and plastic.

The probe head 160 further comprises a grip 170. The grip is designed to be grasped securely by fenestrated laparoscopic graspers 200 (see also FIGS. 3, 4 and 5 which illustrate the grip 170 of the probe head 160 being grasped by the fenestrated laparoscopic graspers 200).

The grip 170 comprises protrusions 140 that are positioned and shaped to enable the grip 170 to be graspable securely by the fenestrated laparoscopic graspers 200 at a first angle relative to the sensing direction of the probe head 160. The protrusions 140 are also positioned and shaped to enable the grip 170 to be graspable securely at a second angle relative to the sensing direction of the probe head 160.

In particular, in the tethered laparoscopic probe 100 of FIGS. 1-5, the protrusions 140 comprise a pair of protrusions positioned such that the first protrusion 140a of the pair of protrusions is graspable by a first jaw 220 of the fenestrated laparoscopic graspers 200 while a second protrusion 140b of the pair of protrusions is graspable by a second jaw 220 of the fenestrated laparoscopic graspers 200. The protrusions 140 are provided by a T-shaped abutment on the grip 170.

FIG. 3 and FIG. 5 show the probe head 160 of the tethered laparoscopic probe 100 being held at a first angle relative to the sensing direction of the probe head 160. As explained above, for demonstrative purposes the sensing direction is considered to be the transversal direction of the elongated casing 180, passing through the aperture 150. The first angle is accordingly substantially 0 degrees. That is, FIGS. 3 and 5 show the probe head 160 of the tethered laparoscopic probe 100 being held at an angle of substantially 0 degrees to the sensing direction of the probe head 160.

The fenestrated laparoscopic graspers 200 comprise two opposable fenestrated jaws 220. Each jaw 220 comprises an oblong slot 210. The first protrusion 140a of the pair of protrusions is shaped and positioned such that, when the tethered laparoscopic probe 100 is grasped at the first angle relative to the sensing direction with the fenestrated laparoscopic graspers 200, the first protrusion 140a engages with a slot 210 and fits snugly within the slot 210 of the first jaw 220 of the fenestrated laparoscopic graspers 200. Similarly, the second protrusion 140b of the pair of protrusions is shaped and positioned such that, when the tethered laparoscopic probe 100 is grasped at the first angle relative to the sensing direction with the fenestrated laparoscopic graspers 200, the second protrusion 140b engages with a slot 210 and fits snugly within the slot 210 of the second jaw 220 of the fenestrated laparoscopic graspers.

Both protrusions 140a and 140b in the example shown in FIGS. 1 to 5 are square-shaped (when viewed from a side angle) with rounded corners, such that when gripped by the fenestrated laparoscopic graspers 200 as shown in FIGS. 3 and 5, parallel edges of the square-shaped protrusions 140a and 140b align with internal faces of the slots 210 of the fenestrated jaws 220. Accordingly, the protrusions 140a and 140b are shaped such that they can be grasped securely by the fenestrated laparoscopic graspers 200, in that, when engaged (jaws 220 are closed), the graspers 200 are substantially restricted from rotating about the protrusions to a different angle relative to the sensing direction.

Advantageously, when the grip 170 is grasped by the fenestrated laparoscopic graspers 200 at the first angle relative to the sensing direction of the probe head 160, the pair of protrusions 140a and 140b restrict angular motion of the fenestrated laparoscopic graspers 200 about the protrusions 140a and 140b and thereby provide greater control to the user of the fenestrated laparoscopic graspers 200 of what direction the tethered laparoscopic probe 100 is directed towards.

The pair of protrusions 140a and 140b are also shaped to be held at an angle of substantially 90 degrees to the sensing direction of the probe head 160 using the fenestrated laparoscopic graspers 200. As shown in FIG. 4, parallel edges of the substantially square-shaped protrusions 140a and 140b align with internal faces of the slots 210 of the fenestrated jaws 220. Accordingly, the protrusions 140a and 140b are shaped such that they can be grasped securely by the fenestrated laparoscopic graspers 200, in that, when engaged, the graspers 200 are substantially restricted from rotating about the protrusions to a different angle relative to the sensing direction.

The shape and position of the protrusions 140a and 140b enable the tethered laparoscopic probe 100 to be grasped at a first angle relative to the sensing direction of the probe head 100 and enable the tethered laparoscopic probe 100 to be grasped at a second angle relative to the sensing direction of the probe head 100. However, to transition from the first angle (FIGS. 3 and 5) to the second angle (FIG. 4), a user of the fenestrated laparoscopic graspers 200 would be required to relax the pressure applied by the fenestrated jaws in order to disengage the jaws 220 from the protrusions 140a and 140b, and then to re-engage with the protrusions 140a and 140b at the second angle.

In order to assist in transitioning from the first angle relative to the sensing direction to the second angle relative to the sensing direction, the probe head is also fitted with a rib 120 suitable for grasping by a surgical instrument, and in particular, by a needle driver, to support the tethered laparoscopic probe 100 while adjusting the angle of attack of the fenestrated laparoscopic graspers 200. In this way, a surgeon or other medical professional using fenestrated laparoscopic graspers 200 to grasp a tethered laparoscopic probe 100 at a first angle relative to the sensing direction is able to adjust their grip by holding the tethered laparoscopic probe 100 by the rib 120 using a needle driver (for example), releasing the pressure on the fenestrated laparoscopic graspers 200 to disengage the slots 210 from the protrusions 140a and 140b and re-engaging with the protrusions at a second angle.

The rib 120 separates two recesses 130a and 130b, which help to define the rib. The skilled person would appreciate that the recesses 130a, 130b need not be present. A rib may protrude/jut out from the probe head 160, but it is desirable for the probe head 160 to have a form factor suitable for passing through a trocar into the cavity.

Figure 6:
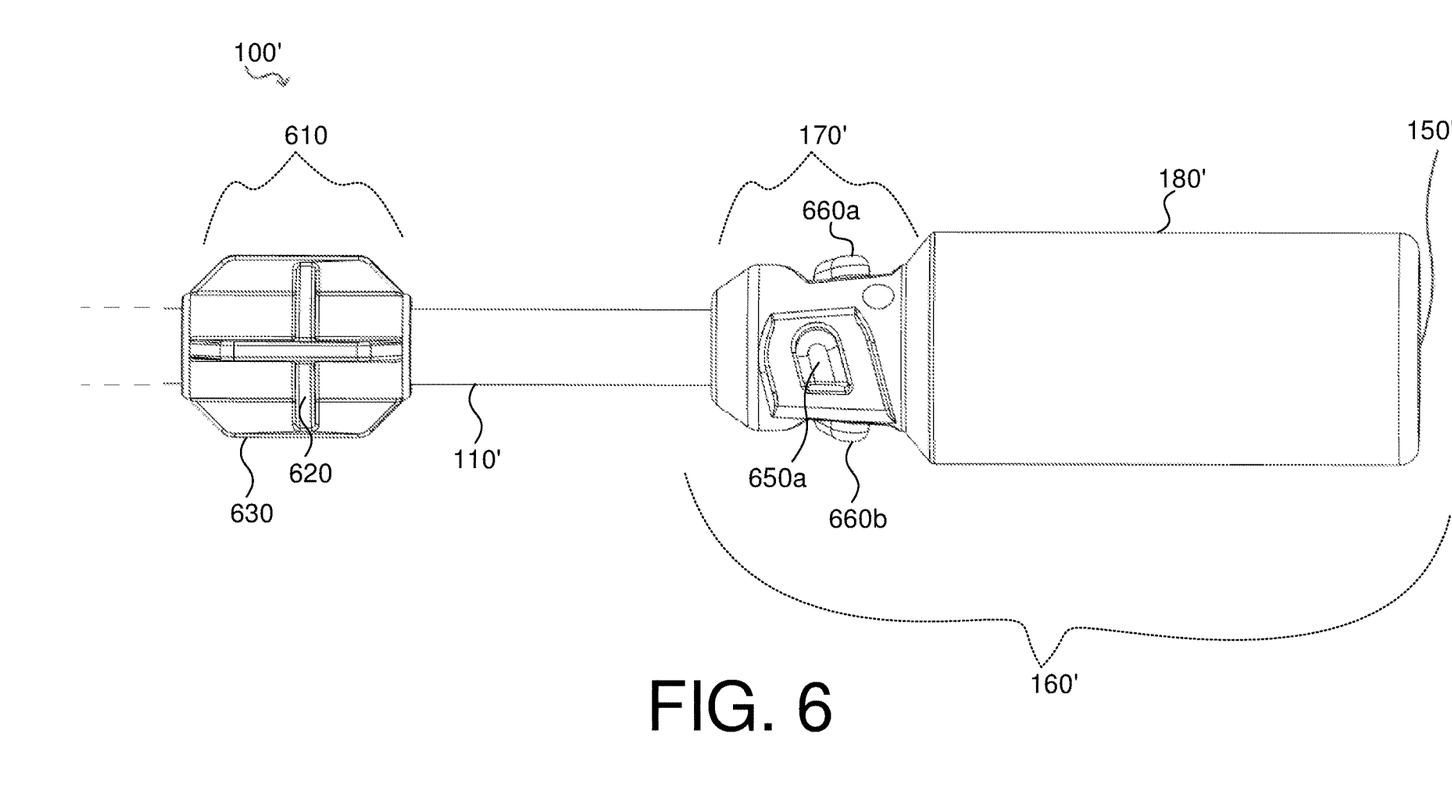
FIG. 6 illustrates a second example of a tethered laparoscopic probe from a first perspective.

FIG. 6 shows a tethered laparoscopic probe 100' according to another example from a first perspective. The tethered laparoscopic probe 100' comprises a probe head 160' and tether 110', which are similar to those described in relation to FIGS. 1 to 5. The probe head 160' once again comprises an elongated casing 180' and a sensor arranged within the casing 160'. The probe head 160' further comprises a grip 170', although the grip 170' is different to the grip 170 of the example shown in FIGS. 1 to 5.

The grip 170' comprises a first pair of protrusions 650 and a second pair of protrusions 660. A first protrusion 650a of the first pair of protrusions 650 is positioned and shaped to be graspable by a first jaw 220 of the fenestrated laparoscopic graspers 200 at a first angle relative to a sensing direction of the tethered laparoscopic probe 100'. A second protrusion 650b of the first pair of protrusions 650 is positioned and shaped to be graspable by a second jaw 220 of the fenestrated laparoscopic graspers 200 at the first angle relative to the sensing direction of the tethered laparoscopic probe 100'. A first protrusion 660a of the second pair of protrusions 660 is positioned and shaped to be graspable by the first jaw 220 of the fenestrated laparoscopic graspers 200 at a second angle relative to a sensing direction of the tethered laparoscopic probe 100'. A second protrusion 660b of the second pair of protrusions 660 is positioned and shaped to be graspable by the second jaw 220 of the fenestrated laparoscopic graspers 200 at the second angle relative to the sensing direction of the tethered laparoscopic probe 100'.

Figure 8A:
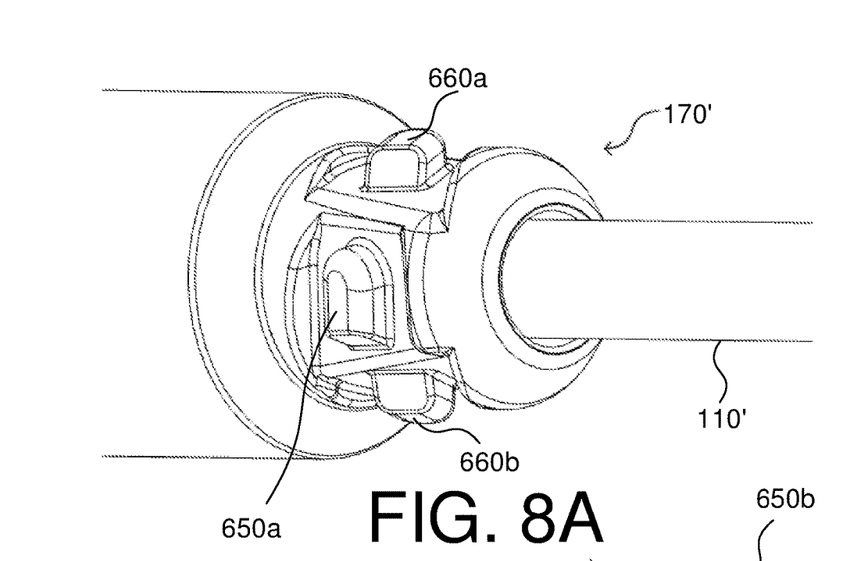
FIGS. 8A, 8B and 8C illustrate a grip of the tethered laparoscopic probe of FIG. 6.
Figure 8B:
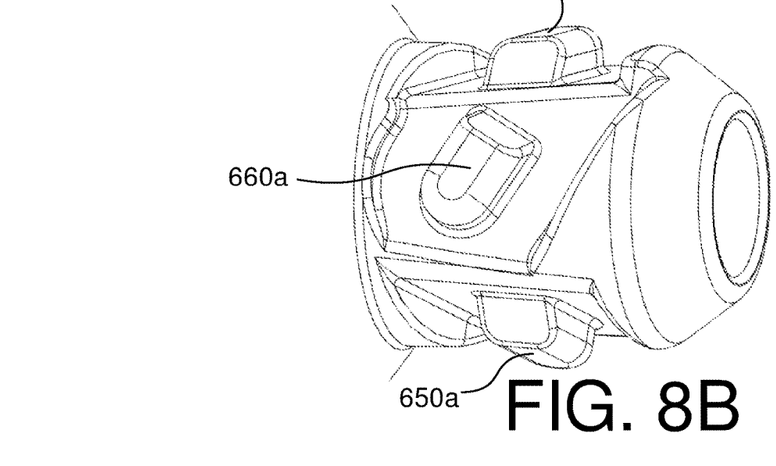
Figure 8C:
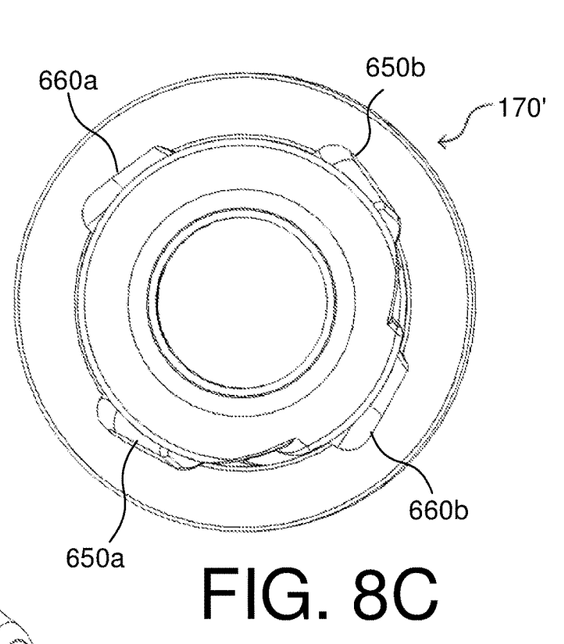

FIG. 8A shows a close-up illustration of the grip 170' fitted to the casing 160'. FIG. 8B shows a close-up illustration of the grip 170' with the casing 160' and the tether removed. FIG. 8C shows the grip 170' from the proximal end of the probe head' (i.e. the distal end of the probe head 160', at which the aperture 150' is located, is seen as extending into the page). As can be seen from these figures, the protrusions 650, 660 are shaped to engage with and fit snugly into the oblong slots of the fenestrated laparoscopic graspers 200. The protrusions 650 and 660 are, in the example of FIGS. 5, 6, 8A, 8B, 8C, 9 and 10 shaped to have two substantially straight and parallel edges and a curved edge to fit an oblong slot 210 of a jaw 220 of the fenestrated laparoscopic graspers 200. In order to grasp the tethered laparoscopic probe 100' at the first angle relative to the sensing direction of the probe head 160', the fenestrated laparoscopic graspers may be positioned such that, when pressure is applied to close the fenestrated jaws 220, the protrusions 650a and 650b of the grip 170' interlock with the oblong slots 210 of the respective first and second fenestrated jaws 220. When the jaws 220 are engaged—i.e. closed around the first pair of protrusions 650, the straight edges of the protrusions 650 help to resist any rotational movement of the fenestrated laparoscopic graspers 200 away from the first angle of engagement. If it is desired to grasp the tethered laparoscopic probe 100' at the second angle relative to the sensing direction of the probe head 160', then the pressure of the jaws 220 can be released and the jaws 220 can be repositioned so as to interlock with the second pair of protrusions 660 when pressure is reapplied as shown in FIG. 10. Once again, so long as pressure is applied with the laparoscopic graspers, the shape of the protrusions 660 resists any rotational movement of the fenestrated laparoscopic graspers 200 away from the angle of engagement.

As would be appreciated by the skilled person, the protrusions 650a, 650b, 660a, 660b may be the same or different shaped so long as they engage with the oblong slots 210 of the fenestrated laparoscopic graspers 200 correctly, that is, so long as they are suitable shaped to secure the angle of the fenestrated laparoscopic graspers relative to the sensing direction of the probe head 160'. For example, the protrusions may be substantially square shaped as in the example of FIG. 1, or may be rectangular shaped.

Figure 9:
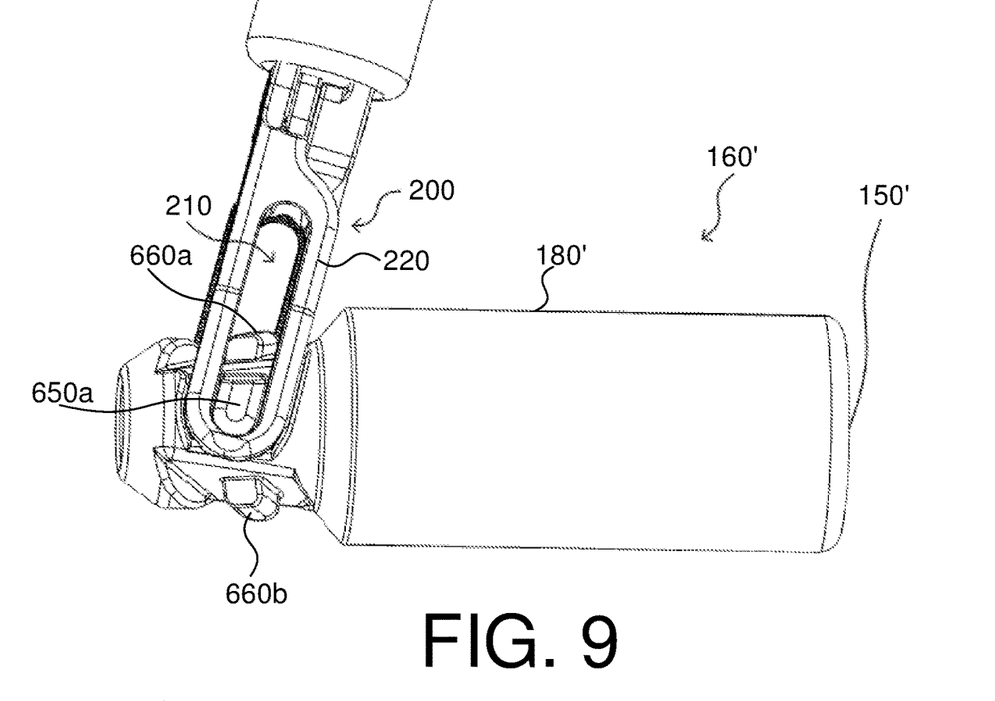
FIG. 9 shows the probe head of the tethered laparoscopic probe of FIG. 6 being held with fenestrated laparoscopic graspers at a first angle.
Figure 10:
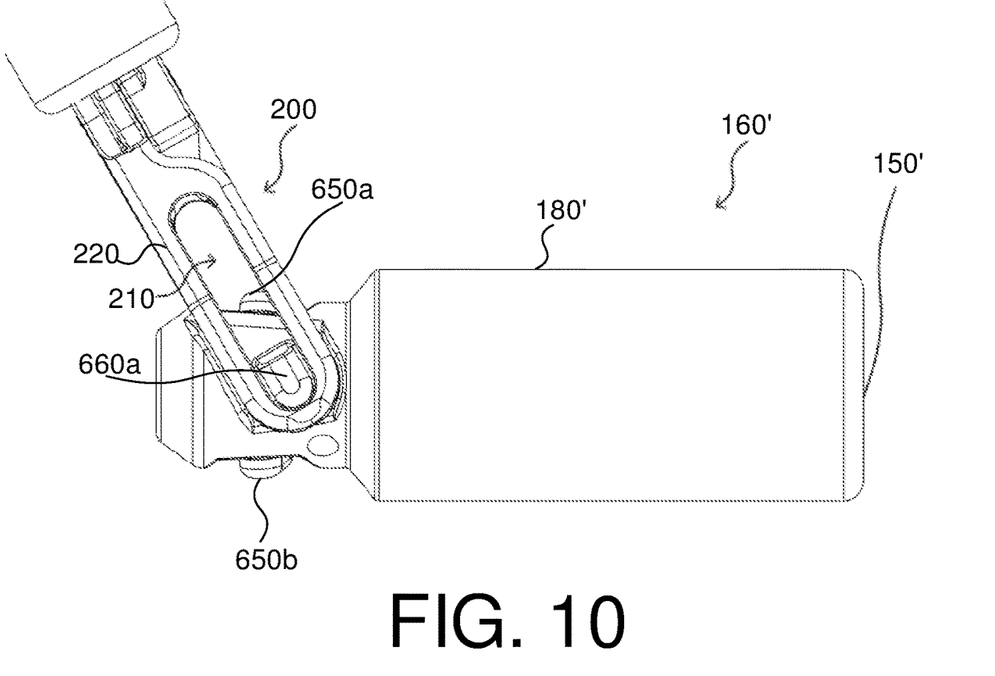
FIG. 10 shows the probe head of the tethered laparoscopic probe of FIG. 6 being held with fenestrated laparoscopic graspers at a second angle.

FIG. 9 illustrates the tethered laparoscopic probe 100' being grasped securely by the fenestrated laparoscopic graspers 200 at the first angle relative to the direction of the probe head 160' (once again, for clarity of illustration, the tether 110' is not shown in FIG. 9). The first angle is substantially 105 degrees.

FIG. 10 illustrates the tethered laparoscopic probe 100' being grasped securely by the fenestrated laparoscopic graspers 200 at the second angle relative to the sensing direction. The second angle is substantially 60 degrees.

As illustrated in FIGS. 6, 7A, 7B and 7C, the tethered laparoscopic probe 100' is also fitted with a collar grip 610. The collar grip 610 is fitted to the tether 110' of the tethered laparoscopic probe 100'. The collar grip 610 comprises a substantially annular through-hole through which the tether 110' extends. The collar grip 610 thereby surrounds a portion of the tether 110'.

Figure 7A:
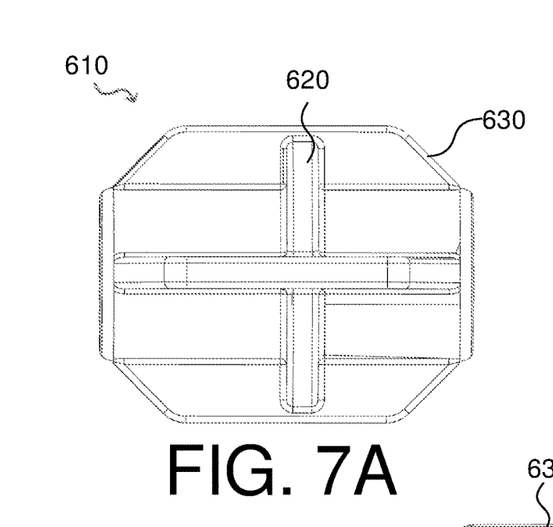
FIGS. 7A, 7B and 7C illustrate a collar grip for use with any tethered laparoscopic probe.
Figure 7B:
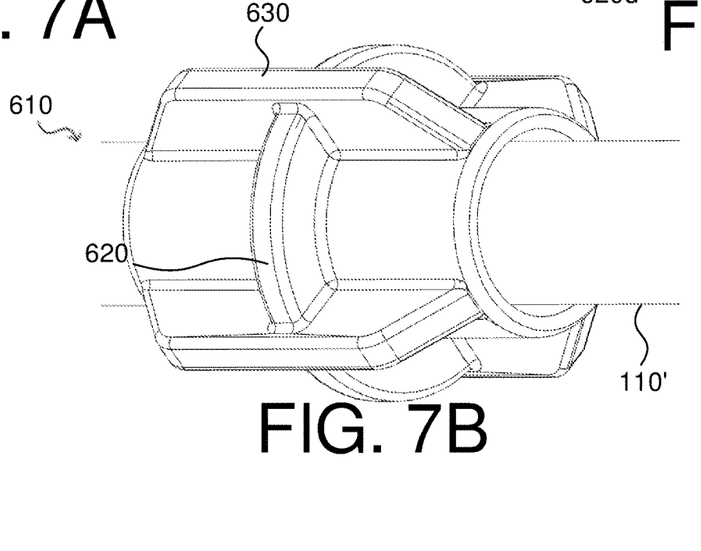
Figure 7C:
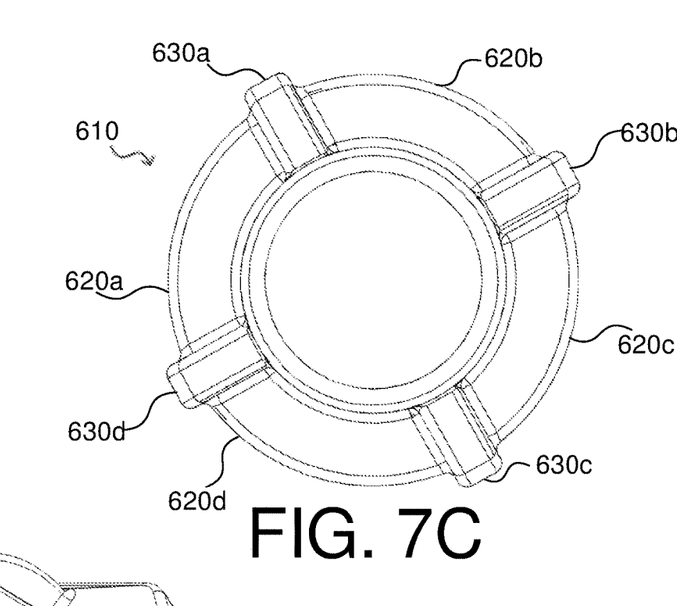

FIG. 7A shows a side view of the collar grip 610. FIG. 7B shows the collar grip 610 along a transverse direction (i.e. with a view centered on the annular through-hole through which the tether 110' (not shown in FIGS. 7A and 7B) extends. FIG. 7C shows the collar grip 610 fitted to the tether 110'.

As can be seen in FIGS. 6, 7A, 7B and 7C, the collar grip 610 comprises a plurality of fins for gripping with a surgical instrument such as a needle driver. A first plurality of fins 620a, 620b, 620c and 620d extend in a radial/axial direction and in a circumferential direction from the collar grip 610. A second plurality of fins 630a, 630b, 630c and 630d extend in a radial/axial direction and in a transversal direction along the length of the collar grip 610.

The collar grip 610 is configured to be used as a secondary grip for the tethered laparoscopic probe 100' that enables improved maneuverability without requiring a user to touch the tether 110' of the probe 100' with a surgical tool, such as a needle driver. Accordingly, the collar grip 610 lessens the risk of damaging the tether 110' while enabling for improved manipulation of the probe 100'.

The architecture of the collar grip 610 may vary. For example, the first plurality of fins may be absent. The first plurality of fins 620 may or may not extend the entire way around the collar grip. A different shaped fin entirely may be used. Similarly, the second plurality of fins 630 may be present or absent and may or may not extend along the entire collar grip 610. Instead of fins, some other grippable feature may be provided on the collar grip 610, for example a rib or bar or other protrusion that can be gripped using jaws of a surgical tool such as a needle driver. The fins enable the collar grip 610 to be gripped by a surgical tool but the exact shape of the fins is not important. The collar grip must when fitted to the tether be of a suitable diameter to pass through a trocar.

Variations of the described embodiments are envisaged, for example, the features of all the described embodiments may be combined in any way.

For example, the collar grip 610 described in relation to the example of the tethered laparoscopic probe 100' in FIGS. 6, 7A, 7B, and 7C may be fitted to any suitable tether, such as tether 110 of the example tethered laparoscopic probe 100 described in relation to FIG. 1. Similarly, the rib 120 and/or the recesses 130a and 130b may be used in conjunction with the example described in relation to FIG. 6.

A tether as described herein may be any suitable connection that may, in use, be used to couple a laparoscopic probe head within the cavity, through the trocar, to the outside world and may be used to, for example, withdraw the probe head from the cavity and ensure that the probe head is not misplaced within the cavity. The tether may take any suitable form, for example the tether may comprise a ribbon or cable. The tether may comprise at least a biocompatible outer layer. The biocompatible outer layer may encompass at least a communication means such as an optical fiber for communicating a signal from the sensor through the trocar to a processor/computing device.

The sensor may be any suitable sensor used for laparoscopic procedures. The sensor may comprise one of a gamma radiation detector, a beta radiation detector, an ultrasound detector. When an ultrasound sensor is used, the windowed aperture may comprise a quarter wavelength index matching layer. The sensor may comprise an optical sensor, for example an optical sensor adapted to detect one or more of visible light, infra-red light, or ultra-violet light. When an optical sensor is used, the laparoscopic probe may further comprise one or more focusing elements, for example a lens or a mirror. The optical sensor may be used for imaging.

The laparoscopic probe 100, 100' may comprise further components. For example, the probe 100, 100' may comprise one or more collimators. The laparoscopic probe may further comprise a biocompatible stand-off for ensuring that the sensor is separated from the subject by a predetermined distance.

It is envisaged that the term "subject" as used herein may be any suitable subject. For example, the subject may be a human or may be an animal. A cavity of the subject may comprise, for example, an abdominal cavity of the subject.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims and drawings).

What is claimed is:

1. A tethered laparoscopic probe for deployment through a trocar into a cavity of a subject, the tethered laparoscopic probe configured to be manipulated by fenestrated laparoscopic graspers comprising opposing fenestrated jaws, the tethered laparoscopic probe comprising:
   a probe head shaped for insertion through the trocar, the probe head comprising:
      an elongated casing;
      a sensor arranged within the casing, the sensor defining a sensing direction of the probe head; and
      a grip for secure grasping by the fenestrated laparoscopic graspers, the grip comprising a pair of protrusions for mating with the fenestrated jaws of the fenestrated laparoscopic graspers, wherein a first protrusion of the pair of protrusions is graspable by a first jaw of the fenestrated laparoscopic graspers while a second protrusion of the pair of protrusions is graspable by a second jaw of the fenestrated laparoscopic graspers; and
   a tether coupled to the probe head and for, in use, tethering the probe head through the trocar;
   wherein the pair of protrusions are positioned and shaped to enable the grip to be grasped securely by the fenestrated laparoscopic graspers at a first angle relative to the sensing direction of the probe head so as to restrict the fenestrated laparoscopic graspers from rotating about the protrusions; and
   wherein the pair of protrusions are positioned and shaped to enable the grip to be grasped securely by the fenestrated laparoscopic graspers at a second angle relative to the sensing direction of the probe head so as to restrict the fenestrated laparoscopic graspers from rotating about the protrusions, the second angle different to the first angle.

2. The tethered laparoscopic probe of claim 1, wherein the protrusions comprise a first pair of protrusions and a second pair of protrusions;
   wherein a first protrusion of the first pair of protrusions is positioned and shaped to be graspable by a first jaw of the fenestrated laparoscopic graspers at the first angle, and a second protrusion of the first pair of protrusions is positioned and shaped to be graspable by a second jaw of the fenestrated laparoscopic graspers at the first angle; and
   wherein a first protrusion of the second pair of protrusions is positioned and shaped to be graspable by the first jaw of the fenestrated laparoscopic graspers at the second angle, and a second protrusion of the second pair of protrusions is positioned and shaped to be graspable by the second jaw of the fenestrated laparoscopic graspers at the second angle.

3. The tethered laparoscopic probe of claim 1, wherein the protrusions are positioned and shaped to enable the grip to be graspable by the fenestrated laparoscopic graspers at a third angle relative to the sensing direction of the probe head, the third angle different to the first angle and the second angle.

4. The tethered laparoscopic probe of claim 1, wherein the grip further comprises a rib, the rib grippable by jaws of a surgical instrument.

5. The tethered laparoscopic probe of claim 4, wherein the rib separates adjacent recesses of the grip.

6. The tethered laparoscopic probe of claim 1, further comprising a collar grip fitted to the tether, the collar grip grippable by jaws of a surgical instrument.

7. The tethered laparoscopic probe of claim 6, wherein the surgical instrument is a needle driver.

8. The tethered laparoscopic probe of claim 1, wherein the sensor comprises a gamma radiation detector configured to detect gamma radiation through an aperture of the casing.

9. The tethered laparoscopic probe of claim 8, wherein the gamma radiation detector comprises a scintillator configured to scintillate in response to received gamma radiation and a photodetector to detect the scintillated light from the scintillator.

10. The tethered laparoscopic probe of claim 8, wherein the gamma radiation detector comprises a semiconductor gamma radiation detector.

11. The tethered laparoscopic probe of claim 1, wherein the sensor comprises a beta radiation detector configured to detect beta radiation through an aperture of the casing.

12. The tethered laparoscopic probe of claim 11, wherein the beta radiation detector comprises a scintillator configured to scintillate in response to received beta radiation and a photodetector to detect the scintillated light from the scintillator.

13. The tethered laparoscopic probe of claim 1, wherein the sensor comprises an ultrasound sensor.

14. The tethered laparoscopic probe of claim 1, wherein the probe head further comprises a second sensor arranged within the casing, the second sensor for sensing through an aperture of the casing.

15. The tethered laparoscopic probe of claim 1, wherein the grip is structurally integral to the casing.

16. A tethered laparoscopic probe for deployment through a trocar into a cavity of a subject, the tethered laparoscopic probe comprising:
   a probe head shaped for insertion through the trocar, the probe head comprising:
      an elongated casing; and
      a sensor arranged within the casing, the sensor defining a sensing direction of the probe head;
      a grip for secure grasping by fenestrated laparoscopic graspers including fenestrated jaws, the grip comprising a pair of protrusions for mating with the fenestrated jaws of the fenestrated laparoscopic graspers, wherein a first protrusion of the pair of protrusions is graspable by a first jaw of the fenestrated laparoscopic graspers while a second protrusion of the pair of protrusions is graspable by a second jaw of the fenestrated laparoscopic graspers; and
   a tether coupled to the probe head and for, in use, tethering the probe head through the trocar;
   wherein the pair of protrusions are positioned and shaped to enable the grip to be grasped securely by the fenestrated laparoscopic graspers at a first angle relative to the sensing direction of the probe head so as to restrict the fenestrated laparoscopic graspers from rotating about the protrusions; and
   wherein the pair of protrusions are positioned and shaped to enable the grip to be grasped securely by the fenestrated laparoscopic graspers at a second angle relative to the sensing direction of the probe head so as to restrict the fenestrated laparoscopic graspers from rotating about the protrusions, the second angle different to the first angle.

17. A kit comprising:
   the tethered laparoscopic probe of claim 1; and
   fenestrated laparoscopic graspers comprising opposing fenestrated jaws, the fenestrated jaws shaped to mate with protrusions of the grip of the tethered laparoscopic probe to securely grasp the tethered laparoscopic probe.

18. The kit of claim 17, wherein the fenestrated laparoscopic graspers are robotically controllable.

19. The kit of claim 17, wherein the fenestrated laparoscopic graspers are manually controllable.

* * * * *